US009523648B2

(12) United States Patent
Urano et al.

(10) Patent No.: US 9,523,648 B2
(45) Date of Patent: Dec. 20, 2016

(54) DEFECT INSPECTION DEVICE AND DEFECT INSPECTION METHOD

(71) Applicant: Hitachi High-Technologies Corporation, Minato-ku, Tokyo (JP)

(72) Inventors: Yuta Urano, Tokyo (JP); Toshifumi Honda, Tokyo (JP); Yukihiro Shibata, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/422,583

(22) PCT Filed: Jul. 29, 2013

(86) PCT No.: PCT/JP2013/070414
§ 371 (c)(1),
(2) Date: Feb. 19, 2015

(87) PCT Pub. No.: WO2014/050292
PCT Pub. Date: Apr. 3, 2014

(65) Prior Publication Data
US 2015/0241361 A1   Aug. 27, 2015

(30) Foreign Application Priority Data

Sep. 28, 2012   (JP) ................. 2012-215484

(51) Int. Cl.
*G01N 21/00*      (2006.01)
*G01N 21/956*     (2006.01)
*G01N 21/95*      (2006.01)

(52) U.S. Cl.
CPC ........ *G01N 21/956* (2013.01); *G01N 21/9501* (2013.01)

(58) Field of Classification Search
USPC ...................... 356/237.1–237.5, 239.1–239.8
See application file for complete search history.

(56) References Cited

U.S. PATENT DOCUMENTS

| 5,719,405 A | 2/1998 | Hayano |
| 5,774,222 A | 6/1998 | Maeda et al. |

(Continued)

FOREIGN PATENT DOCUMENTS

| JP | 2-38951 A | 2/1990 |
| JP | 7-83843 A | 3/1995 |

(Continued)

OTHER PUBLICATIONS

Corresponding International Search Report dated Sep. 24, 2013 with English translation dated (five (5) pages).

*Primary Examiner* — Tri T Ton
(74) *Attorney, Agent, or Firm* — Crowell & Moring LLP

(57) ABSTRACT

A defect-inspection device includes an irradiation unit having an objective-pupil-optical unit that allows illumination light linearly condensed by a first light-condensing unit to pass through, and an objective lens that allows the illumination light having passed through the objective-pupil-optical unit to pass through; an irradiation-position-control unit that controls a passing position of the illumination light in the objective-pupil-optical unit disposed at a pupil surface of the objective lens; a detection unit having a second light-condensing unit that condenses light irradiated by the irradiation unit and generated from a sample, a specular-reflection light-blocking unit that blocks specular-reflection light from the sample and light components generated near the pupil surface among the light beams condensed by the second light-condensing unit, and an image-forming unit that images the light that is condensed by the second light-condensing unit and is not blocked by the specular-reflection light-blocking unit into a detector; and a defect-determination unit that detects a defect on a surface of the sample on the basis of a signal of the image imaged by the image-forming unit.

8 Claims, 8 Drawing Sheets

(56) References Cited

U.S. PATENT DOCUMENTS

| | | | |
|---|---|---|---|
| 6,800,859 | B1 | 10/2004 | Shishido et al. |
| 8,111,406 | B2 * | 2/2012 | Hidaka ................ G03F 9/7034 |
| | | | 356/614 |
| 8,274,652 | B2 | 9/2012 | Urano et al. |
| 2006/0262297 | A1 | 11/2006 | Matsui et al. |
| 2008/0165343 | A1 | 7/2008 | Lewis et al. |
| 2009/0296096 | A1 | 12/2009 | Jeong |
| 2012/0268742 | A1 * | 10/2012 | Hatano ................ G01N 21/956 |
| | | | 356/364 |
| 2012/0281207 | A1 * | 11/2012 | Yoshimizu ......... G01N 21/9501 |
| | | | 356/237.5 |

FOREIGN PATENT DOCUMENTS

| | | |
|---|---|---|
| JP | 8-162511 A | 6/1996 |
| JP | 10-68698 A | 3/1998 |
| JP | 2000-193443 A | 7/2000 |
| JP | 2006-329630 A | 12/2006 |
| JP | 2010-271186 A | 12/2010 |
| JP | 2011-523711 A | 8/2011 |
| JP | 4838122 B2 | 12/2011 |
| JP | 2012-68261 A | 4/2012 |
| WO | WO 2011/010425 A1 | 1/2011 |

* cited by examiner

FIG. 5
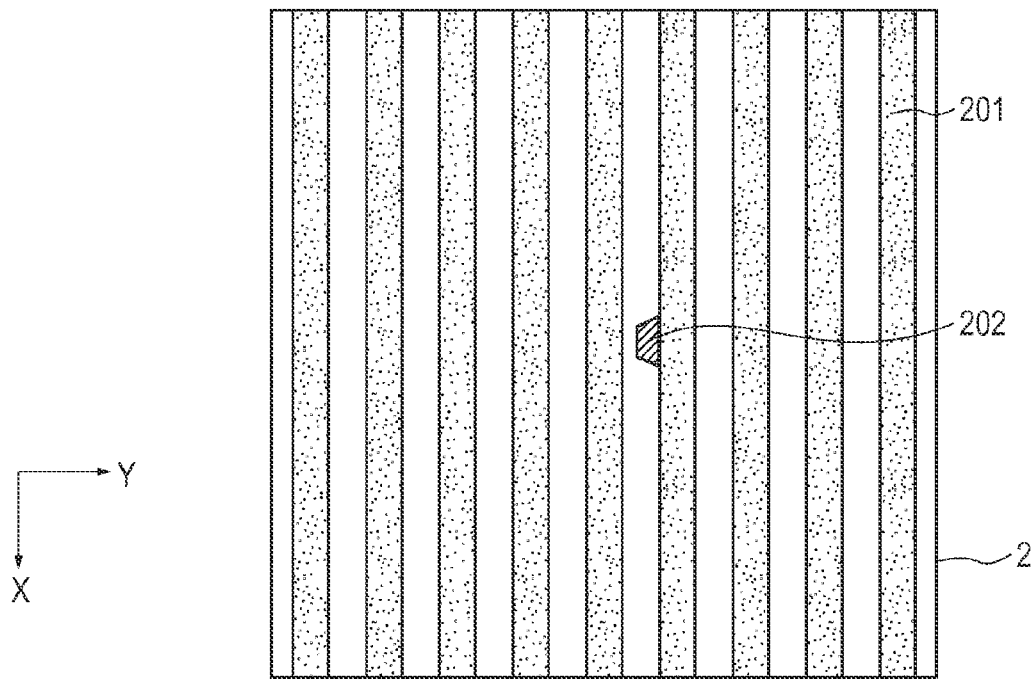
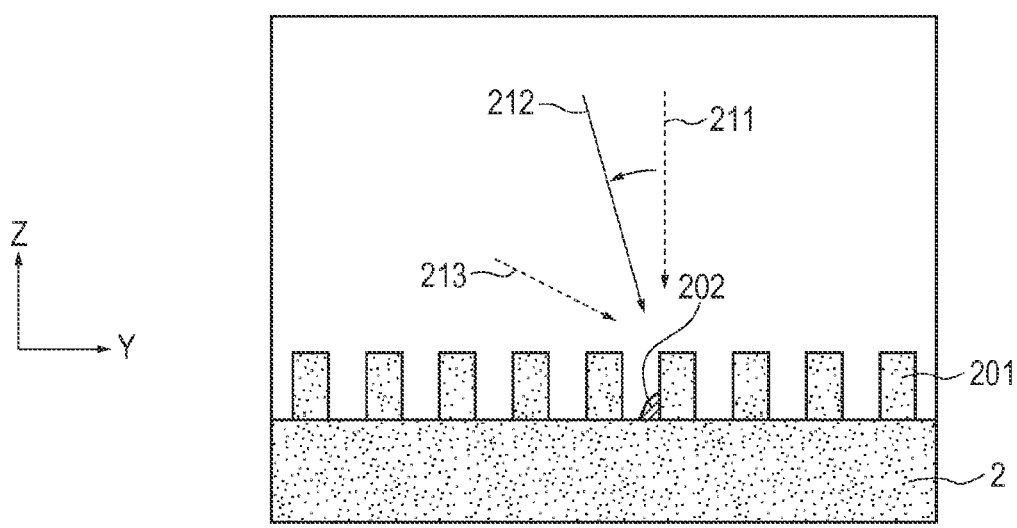

DEFECT INSPECTION DEVICE AND DEFECT INSPECTION METHOD

TECHNICAL FIELD

The present invention relates to a defect inspection device and a defect inspection method in which a defect generation status is inspected in a manufacturing process of applying countermeasures after detecting and analyzing defects generated in a manufacturing process such as a semiconductor manufacturing process, a liquid crystal display element manufacturing process, or a printed circuit board manufacturing process in which a pattern is formed on a substrate to produce an object.

BACKGROUND ART

Japanese Patent No. 4838122 (Patent Literature 1) is one of background arts in the technical field. The patent publication describes "an optical apparatus comprising: a second optical device which focuses a radiation light ray on a second focused light ray at a second incidence angle corresponding to the vertical direction or substantially the vertical direction relative to an illuminated area on a surface of a sample and the second incidence angle of which is different from a first incidence angle; an elongated reflection surface that reflects a radiation ray in the light ray focused by the second optical device to the illuminated area on the surface of the sample; a first detector array; and a light-condensing optical device which condenses the radiation ray generated from the first and/or second focused light rays and scattered or reflected from a first line and/or the illuminated area on the surface of the sample, which focuses the radiation ray condensed from parts of the line and/or the illuminated area on a corresponding detector in the first array, and which blocks the radiation ray in the light ray that is focused by the second optical device and that is mirror-reflected on the illuminated area on the surface of the sample from reaching the first detector array by using the elongated reflection surface" (claim 1).

CITATION LIST

Patent Literature

Patent Literature 1: Japanese Patent No. 4838122

SUMMARY OF INVENTION

Technical Problem

In an optical dark-field defect inspection, vertical illumination that enters from the normal line direction of an inspection target surface is not effective in some cases depending on the type of a defect, the directionality of a defect shape, or the directionality of a background pattern.

As a concrete example, part of an illumination light flux is blocked by a background pattern, and the illumination light does not sufficiently reach a defect. Thus, sufficient scattered light from the defect cannot be obtained, and the defect cannot be detected with a high degree of sensitivity.

Further, a phenomenon in which the brightness of the background pattern is leaked around the background pattern at an end of the background pattern that is brightly detected is observed, and thus a defect located near the background pattern that is brightly detected cannot be detected with a high degree of sensitivity.

Further, in the case where dark-field detection is carried out using TTL (Through The Lens) illumination in which illumination light is allowed to vertically enter an inspection target through a vertical-detection objective lens that detects from the normal line direction of an inspection target surface, a mirror disposed at the pupil position of the objective lens guides the illumination light in the inspection target direction, and the mirror serves to block specular reflection light that is returned from the inspection target surface. In this case, it is difficult to arbitrarily adjust the width of a light-blocking unit that blocks the specular reflection light, and thus the optimum detection aperture conditions cannot be set for the inspection target.

Solution to Problem

In order to solve the above-described problems, the present invention employs, for example, configurations described in Claims.

The present application includes plural units to solve the above-described problems. One example is a defect inspection device including: an irradiation unit having a light source that emits a laser beam, a first light-condensing unit that linearly condenses the laser beam emitted from the light source, an objective pupil optical unit that allows the illumination light linearly condensed by the first light-condensing unit to pass through, and an objective lens that allows the illumination light having passed through the objective pupil optical unit to pass through; an irradiation position control unit that controls a passing position of the illumination light in the objective pupil optical unit disposed at a pupil surface of the objective lens; a detection unit having a second light-condensing unit that condenses light irradiated by the irradiation unit and generated from a sample, a specular reflection light-blocking unit that blocks specular reflection light from the sample and light components generated near the above of the pupil surface among the light beams condensed by the second light-condensing unit, and an image forming unit that images the light that is condensed by the second light-condensing unit and that is not blocked by the specular reflection light-blocking unit into a detector; and a defect determination unit that detects a defect on a surface of the sample on the basis of a signal of the image imaged by the image forming unit.

Advantageous Effects of Invention

According to the present invention, defects with various characteristics can be inspected with a high degree of sensitivity. Problems, configurations, and effects other than those described above will be clarified by the following description of an embodiment.

BRIEF DESCRIPTION OF DRAWINGS

FIG. 5 shows an example of an illumination method in which light enters from a direction inclined relative to the normal line direction of an inspection target in order to detect a defect with a high degree of sensitivity.

DESCRIPTION OF EMBODIMENTS

The embodiment describes an example of a defect inspection device that inspects a defect generation status in a manufacturing process of applying countermeasures after detecting and analyzing defects generated in a manufacturing process such as a semiconductor manufacturing process, a liquid crystal display element manufacturing process, or a printed circuit board manufacturing process in which a pattern is formed on a substrate to produce an object.

Figure 1:
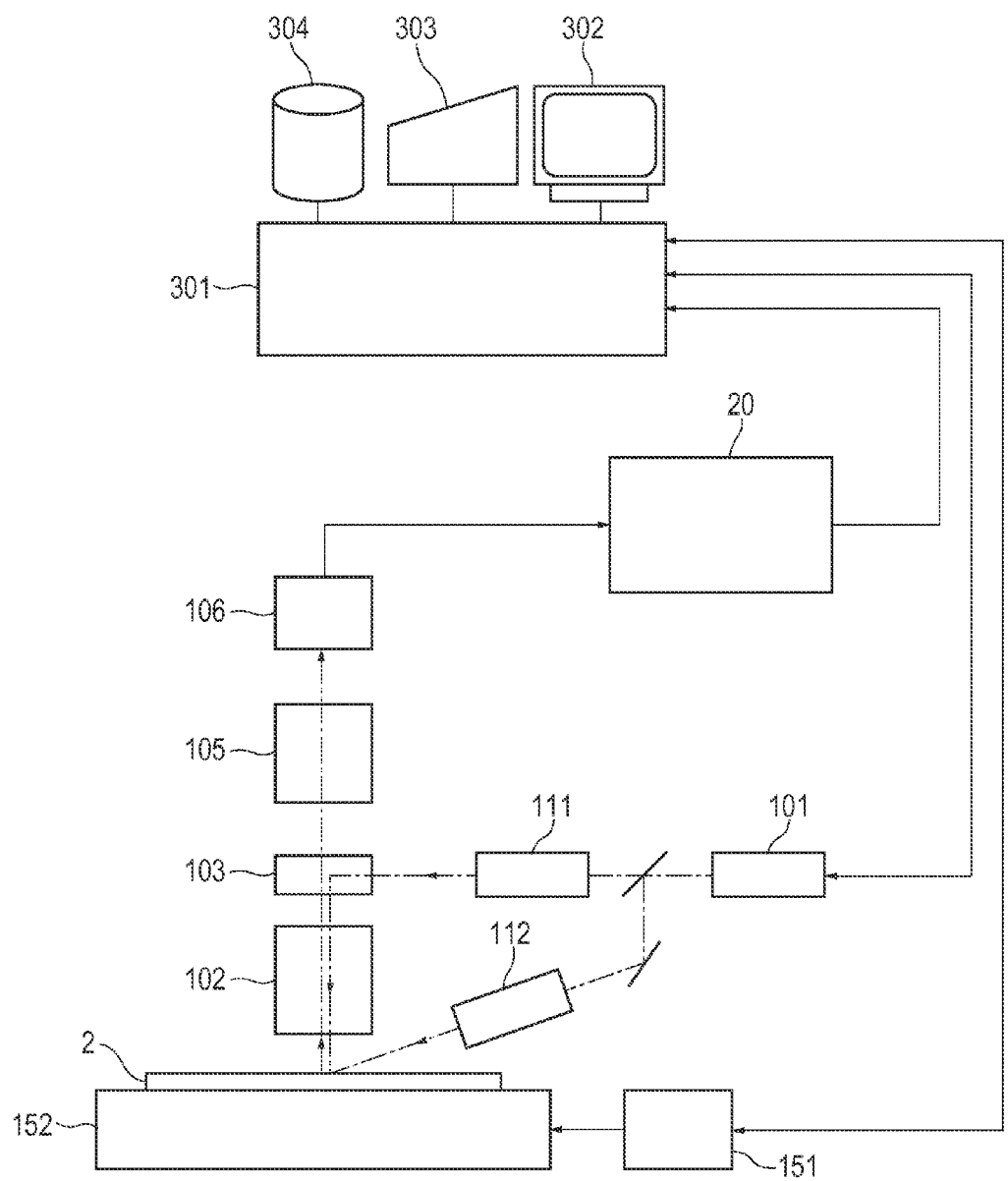
FIG. 1 shows an example of a configuration of a defect inspection device according to the present invention.

FIG. 1 shows an example of a configuration of a defect inspection device in the embodiment. The device shown in FIG. 1 is configured using a light source unit 101, a TTL illumination unit 111, an oblique illumination unit 112, an objective lens 102, an objective pupil optical unit 103, an image forming lens 105, a detector 106, a processing unit 20, an entire control unit 301, a display unit 302, a computing unit 303, a memory unit 304, a stage driving unit 151, and an X-Y-Z-θ stage 152 (hereinafter, referred to as a stage 152).

An outline of operations of the defect inspection device according to the present invention shown in FIG. 1 will be described. Illumination light is irradiated onto an inspection target substrate 2 by the light source unit 101, the TTL illumination unit 111, the objective pupil optical unit 103, and the objective lens 102. Illumination light is simultaneously or separately irradiated onto the inspection target substrate 2 by the light source unit 101 and the oblique illumination unit 112. Reflected light, diffracted light, and scattered light generated from the inspection target substrate 2 are condensed by the objective lens 102, and then converted into electric signals by the detector 106 through the objective pupil optical unit 103 and the image forming lens 105. A defect is determined in the processing unit 20 on the basis of the obtained electric signals. The determination result is stored in the memory unit 304 and displayed on the display unit 302 through the entire control unit 301. The inspection target substrate 2 is scanned by the stage 152 driven by the stage driving unit 151, and the entire surface is inspected.

The light source unit 101 includes a laser light source, an attenuator, an ND filter, a wave plate, and a beam expander (not shown). In the light source unit 101, illumination light with the amount of light, the polarization state, the beam diameter and the shape adjusted and controlled is generated, and is guided to the TTL illumination unit 111 and the oblique illumination unit 112. A short-wavelength, high-power, high-brightness, and highly stabilized laser light source is suitable, and a third, fourth, or fifth harmonic laser light source of a YAG laser is used.

FIG. 1 illustrates only one detection unit that is configured using the objective lens 102, the objective pupil optical unit 103, the image forming lens 105, and the detector 106. However, plural detection units maybe installed at positions where the objective lenses thereof do not mechanically interfere with each other. The processing unit 20 processes signals detected by plural detection units to determine the defect.

Figure 2:
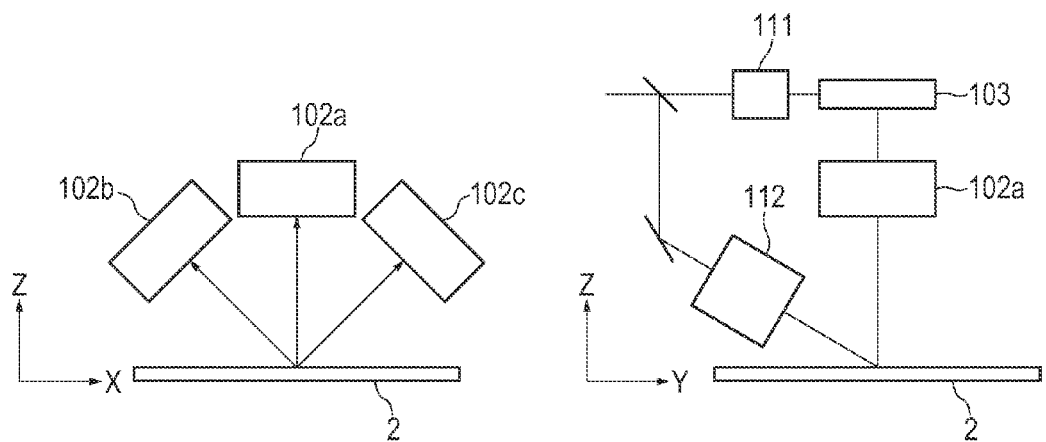
FIG. 2 shows an example of a positional relation among an oblique illumination unit, a TTL illumination unit, and respective objective lenses of plural detection units.

FIG. 2 is a diagram for showing an example of a positional relation among the oblique illumination unit 112 and respective objective lenses 102a, 102b, and 102c of plural detection units. A plane including the inspection target substrate 2 is referred to as an XY plane, and the normal line direction of the inspection target substrate 2 is referred to as a Z direction. The primary scanning direction of the stage is referred to as an X direction, and the secondary scanning direction is referred to as a Y direction. The objective lenses 102a, 102b, and 102c associated with three detection units have optical axes in the XZ plane. The objective lens 102a is disposed in the Z direction to detect light emitted in the Z direction (vertical detection unit). The objective lenses 102b and 102c are disposed on the both sides of the objective lens 102a to detect light emitted in directions inclined from the Z direction (oblique detection unit).

The illumination light is guided to the TTL illumination unit 111 or the oblique illumination unit 112 by loading or unloading a mirror. Using a beam splitter that branches an optical path in place of the mirror, the illumination light can be guided to the both of the TTL illumination unit 111 and the oblique illumination unit 112. The illumination light having passed through the TTL illumination unit 111 is guided to the objective pupil optical unit 103 disposed at the pupil position of the objective lens 102a, and is then guided to the inspection target substrate 2 through the objective lens 102a. The illumination light having passed through the oblique illumination unit 112 travels outside the objective lens 102a in the YZ plane to be guided to the inspection target substrate 2. The illumination light is condensed on the surface of the inspection target substrate 2 by the above-described optical system in a linear beam shape that is long in the Y direction and short in the X direction. The fields of view of the plural detection units are focused on the light-condensed position of the illumination light.

Figure 3:
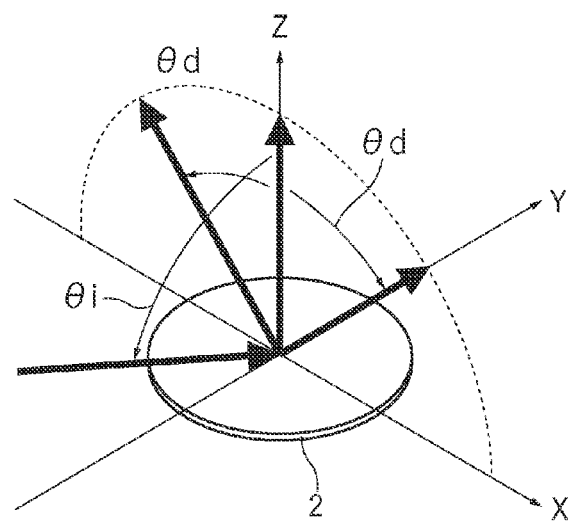
FIG. 3 shows an example of a relation among the incidence direction of oblique illumination and the detection directions of plural detection units.

FIG. 3 shows a relation among the incidence direction of the oblique illumination and the detection directions of the plural detection units. The incidence angle of the oblique illumination is referred to as θi, and the detection angles of the oblique detection units that detect in directions inclined from the normal line of the inspection target substrate are referred to as θd. Two oblique detection units are disposed in directions (±θd) that are symmetric to each other with the YZ plane as a reference.

Figure 4:
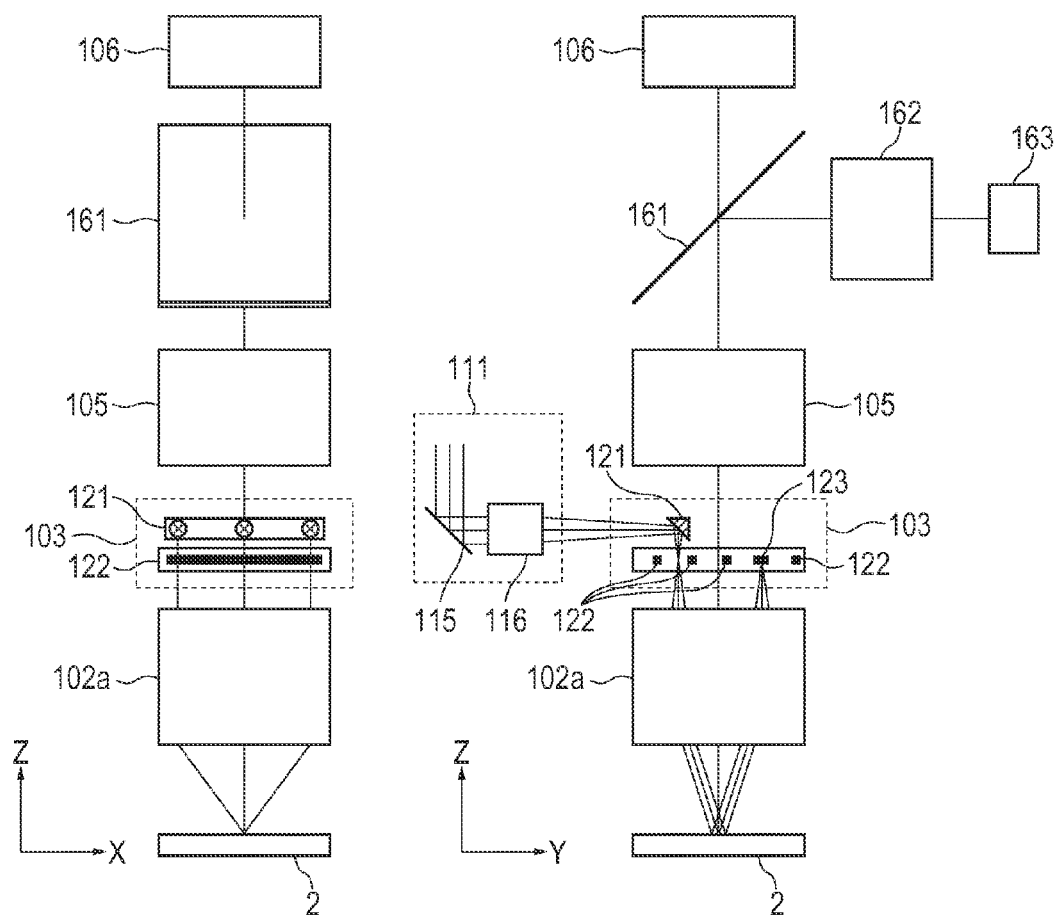
FIG. 4 shows an example of a configuration of a vertical detection unit.

FIG. 4 shows a configuration of the vertical detection unit. The left drawing of FIG. 4 is a cross-sectional view of the vertical detection unit on the XZ plane, and the right drawing of FIG. 4 is a cross-sectional view of the vertical detection unit in the YZ plane.

The TTL illumination unit 111 includes a mirror 115 and a cylindrical lens 116. The objective pupil optical unit 103 includes a TTL illumination mirror 121, a spatial filter 122, and a polarizer (not shown). The TTL illumination mirror 121 is a mirror having a shape long in the X direction. The illumination light is condensed on the pupil surface of the objective lens 102a by the TTL illumination unit 111 and the TTL illumination mirror 121 in a shape long in the X direction. The illumination light having passed through the pupil surface is condensed on the inspection target substrate 2 by the objective lens 102a in a shape long in the Y direction. Specular reflection light of the inspection target substrate 2 passes through the objective lens 102a, and is blocked by a specular reflection light filter 123 provided in the spatial filter 122. Part of light scattered or diffracted by the inspection target substrate 2 and directed to the objective lens 102a is blocked by the spatial filter 122, and then is imaged in the detector 106 by the image forming lens 105 to be detected as an image signal.

The vertical detection unit includes a pupil detection system having a beam splitter 161, a lens system 162, and a pupil detector 163. A signal of the pupil detector 163 is input to the entire control unit 301. The beam splitter 161 can be inserted or removed into/from the optical path. The lens system 162 is configured to image the pupil surface in the pupil detector 163. The image of the surface of the inspection target substrate and the image of the pupil surface can be simultaneously obtained by the pupil detection system.

The TTL illumination mirror 121 includes a position adjusting mechanism, and can be moved in the Y direction. By changing the position of the TTL illumination mirror 121 in the Y direction, the incidence angle of the TTL illumination to the inspection target substrate can be changed within the range of the aperture angle of the objective lens 102a. When the position of the TTL illumination mirror 121 in the Y direction is changed, the position of the cylindrical lens 116 is adjusted together so that the light-condensed position of the illumination light on the inspection target is not changed. This is possible by moving the cylindrical lens 116 in the Y direction by the same distance.

In the configuration shown in FIG. 4, the spatial filter 122 is installed on the pupil surface, and the TTL illumination mirror 121 is installed at a position offset from the pupil surface. Accordingly, no illumination light is linearly condensed on the reflection surface of the TTL illumination mirror 121, and thus the density of illumination power on the reflection surface is reduced as compared to a case of being installed on the pupil surface. In addition, the TTL illumination mirror 121 can be prevented from being deteriorated, and the inspection performance can be stabilized over a long period.

Each of the TTL illumination mirror 121 and the cylindrical lens 116 includes a micro angle rotation mechanism that rotates about the Y axis, and the position of the beam in the X direction linearly condensed on the inspection target substrate can be finely adjusted. Using the adjusting mechanisms, the positions of the fields of view of plural detection units, the light-condensed position of the oblique illumination, and the light-condensed position of the TTL illumination can be easily focused on the inspection target substrate.

The specular reflection light filter 123 blocks light of a long band-like area in the X direction. The specular reflection light filter 123 is installed at a position on the pupil surface where the specular reflection light from the inspection target substrate is blocked. The spatial filter 122 blocks light of plural long band-like areas in the X direction. The spatial filter 122 is installed at a position on the pupil surface where the diffracted light from the inspection target substrate is blocked. Each filter is configured using a plate or a rod made of metal material that block light having the wavelength of illumination light, and includes a position adjusting mechanism that can adjust the light-blocking position. The specular reflection light-blocking filter 123 can control the light-blocking width in the Y direction. The light-blocking width can be controlled by overlapping plural light-blocking filters with each other or by replacing plural light-blocking filters having different light-blocking widths with each other.

It should be noted that as a light-blocking filter, a spatial light modulation element such as a liquid crystal filter, a magnetooptic element, or a micromirror array (MEMS) that can control the shape of the light-blocking area using an electric signal may be used.

In the case where the incidence angle of the TTL illumination is changed, the positions of the specular reflection light filter 123 and the spatial filter 122 are accordingly adjusted. Specifically, the specular reflection light filter 123 is installed at a position symmetric to the position on the pupil surface through which the TTL illumination passes with the optical axis of the objective lens 102a as a reference. Namely, the specular reflection light filter 123 is moved only by the same distance in the direction opposed to the position through which the illumination light passes. The position of the spatial filter 122 is moved while following the specular reflection light filter 123.

Changing the light-blocking width of the specular reflection light filter 123 depending on the shape of a defect is effective in a high-sensitivity inspection. For example, scattered light from a defect with a low spatial frequency is biased near the specular reflection light on the pupil surface. Thus, the signal-to-noise ratio of a defect signal can be increased by narrowing the light-blocking width. Further, it is also effective in a high-sensitivity inspection to change the light-blocking width of the specular reflection light filter 123 depending on the roughness of a background pattern or the roughness on the surface of the substrate that is a noise factor in the inspection. For example, in the case where the degree of the roughness (Ra or RMS) is small or the spatial frequency of the roughness is low (for example, FEOL (Front End of Line) of a semiconductor preceding process or a transistor process), the scattered light from the roughness gather near the specular reflection light on the pupil surface. Thus, noise can be sufficiently cut with a narrow light-blocking width. On the other hand, in the case where the degree of the roughness is large (for example, BEOL (Back End of Line) of a semiconductor preceding process or a wiring process), or the spatial frequency of the roughness is high, the scattered light from the roughness expands in a relatively wide range around the specular reflection light on the pupil surface. Thus, noise can be effectively reduced by widening the light-blocking width.

FIG. 5 shows an example of an illumination method in which light enters from a direction inclined relative to the normal line direction of the inspection target in order to detect a defect with a high degree of sensitivity. FIG. 5 shows a state in which a short-circuit defect 202 is generated on an L&S pattern 201 formed on the inspection target substrate 2. The size of the short-circuit defect 202 is small in the drawing, and thus the L&S pattern is not short-circuited in a strict sense. However, there is a risk of occurrence of a leak, and the short-circuit defect 202 is shown as potential of occurrence of complete short-circuit. Thus, it is necessary to detect as a defect.

As shown in FIG. 5, in the case where vertical illumination 211 is carried out from the normal line direction of the inspection target substrate relative to the defect attached to the side of the L&S pattern 201, about the half of the illumination light flux is blocked by the L&S pattern. Thus, the scattered light from the short-circuit defect 202 disadvantageously becomes small. Further, as shown in the YZ cross-sectional view of FIG. 5, even in the case where oblique illumination 213 that enters from the outside of the objective lens is carried out with respect to the defect the height of which is shorter than that of the L&S pattern 201, the illumination light enters at a small elevation angle, and the short-circuit defect 202 is hidden behind the L&S pattern. Thus, the scattered light from the defect disadvantageously becomes small. By using the TTL illumination 212 inclined from the vertical direction in the YZ plane, the illumination can be allowed to more effectively reach the short-circuit defect 202, high-intensity scattered light can be generated, and a high sensitive degree of defect detection can be obtained. Further, in the case of a defect shape in which the dimension in the Z direction is larger than that in the Y direction as shown in FIG. 5, the area of the defect anticipated from the direction 212 inclined from the vertical direction is larger than that of the defect anticipated from the vertical direction 211. Thus, the scattering cross-section of the defect by the incidence of the illumination light from the direction 212 inclined from the vertical direction becomes large, and a large defect scattered light signal can be obtained.

Figure 6:
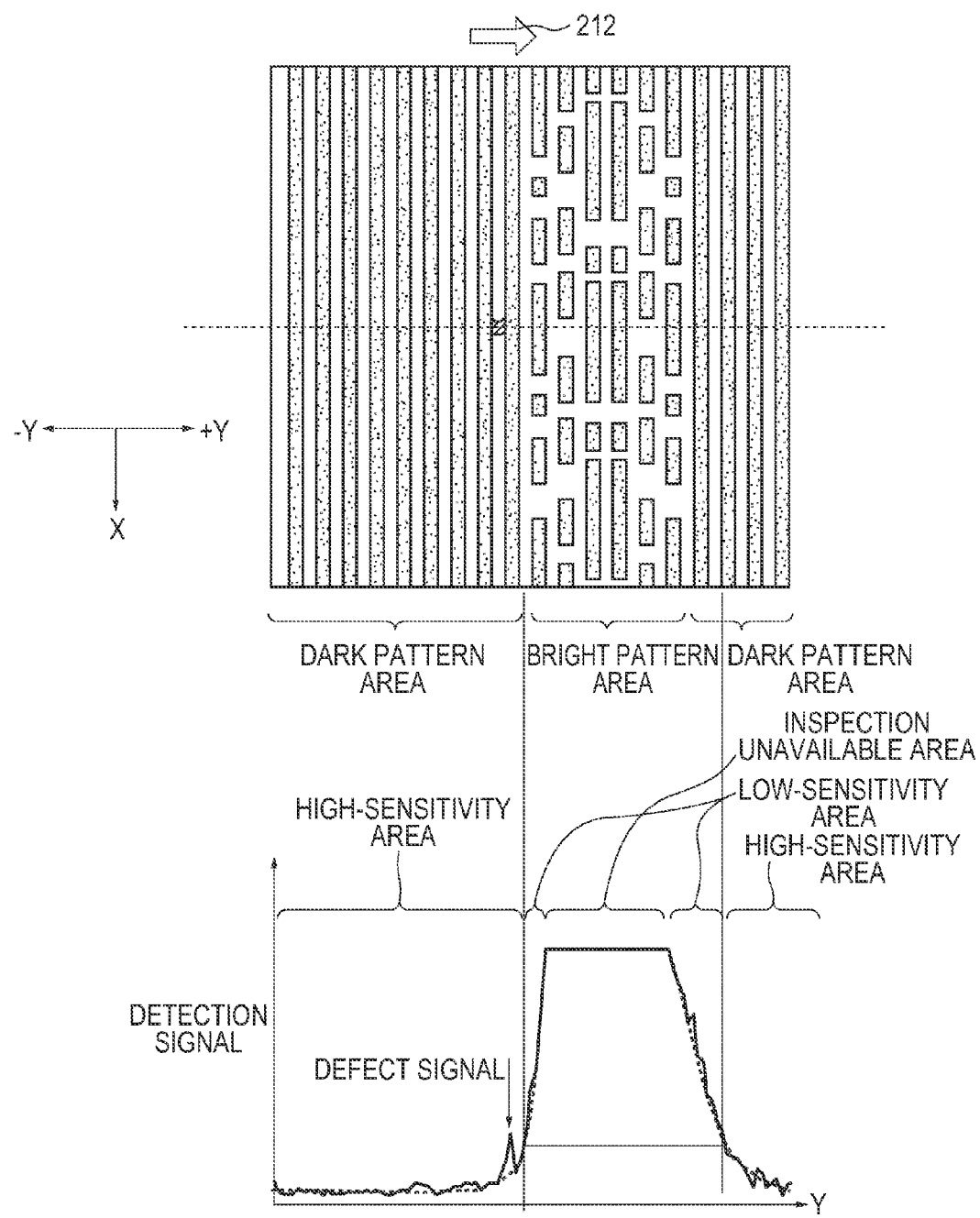
FIG. 6 shows another example of an illumination method in which light enters from a direction inclined relative to the normal line direction of the inspection target in order to detect a defect with a high degree of sensitivity.

FIG. 6 shows another example of an illumination method in which light enters from a direction inclined relative to the normal line direction of the inspection target in order to detect a defect with a high degree of sensitivity. In a dark-field defect inspection, diffracted light from a pattern does not enter the detector in an area where the pattern is regularly repeated with short cycles, or the diffracted light from the pattern can be easily blocked by the spatial filter 122. Thus, the area is detected as a dark pattern (dark pattern area), and noise caused by the pattern can be suppressed to a low level. Accordingly, a high-sensitivity inspection can be realized. On the other hand, in an area where a pattern with long cycles or with less regularity is formed, it is difficult to reduce the diffracted light, and thus the area is detected as a bright pattern (bright pattern area). In addition, noise caused by the pattern is large, or the detector is saturated. Accordingly, it is difficult to conduct a high-sensitivity inspection. The periodicity of the pattern is interrupted at an end of the dark pattern area. Thus, abnormality or failure is likely to occur in the pattern formation using the optical lithography, and defects are easily generated. In the case where the bright pattern area exists near the dark pattern area, a phenomenon in which the brightness of the bright pattern expands and is increased around the bright pattern can be observed due to the limit of the spatial resolution of the detection optical system. Thus, the sensitivity at an end of the dark pattern area is reduced. In the case of the vertical illumination, this phenomenon occurs at the both ends of the bright pattern in the Y direction due to the symmetry.

As shown in FIG. 6, the TTL illumination mirror is allowed to be shifted on the −Y direction side relative to the optical axis of the objective lens 102a, and the incidence direction of the TTL illumination is allowed to be inclined so as to have a vector component directed from the −Y direction to the +Y direction. Accordingly, the bright pattern can be prevented from being largely expanded on the −Y direction side of the bright pattern. Thus, a defect of the dark pattern area near the −Y direction side of the bright pattern can be detected with a high degree of sensitivity. As a side effect, there occurs a phenomenon in which the bright pattern is largely expanded on the +Y direction side of the bright pattern. As a countermeasure, the inspection target 2 is inspected by rotating 180 degrees while keeping the inclined direction of the TTL illumination, or the inspection target 2 is inspected by inverting the inclined direction of the TTL illumination, so that a defect of the dark pattern area near the +Y direction side of the bright pattern can be detected with a high degree of sensitivity.

Figure 7:
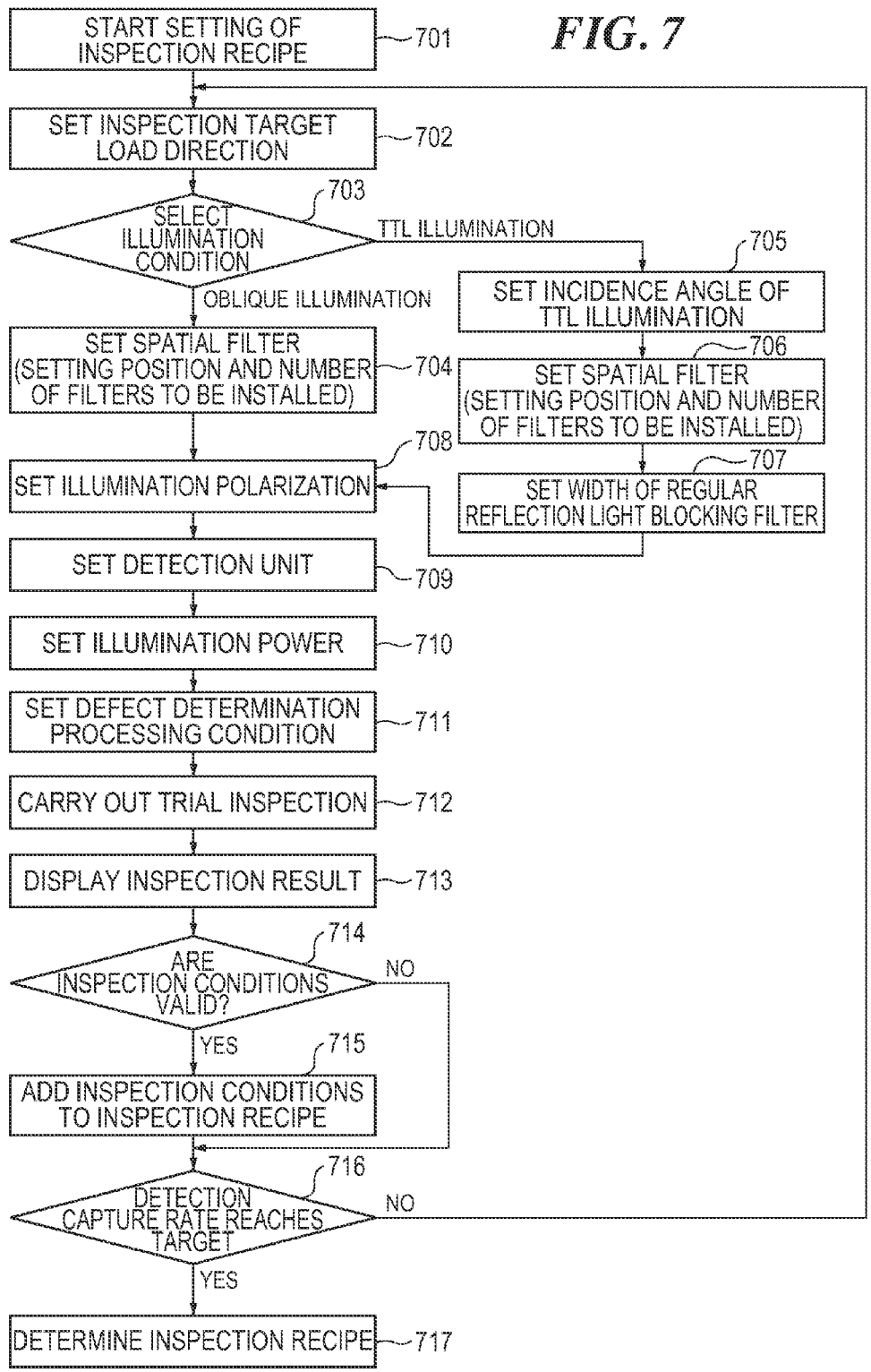
FIG. 7 shows an example of a flow chart of setting an inspection recipe.

FIG. 7 shows a flow chart of setting an inspection recipe. In this case, the inspection recipe refers to inspection conditions (illumination conditions, detection conditions, and defect determination processing conditions) under which the inspection is carried out, or a combination of plural inspection conditions. In the case where the inspection is carried out while combining plural inspection conditions, the inspection is sequentially carried out under each inspection condition, and the inspection results obtained in the respective inspections are integrated to obtain a final inspection result.

The setting of the inspection recipe is started (S701), and the load direction of the inspection target substrate is set (S702). The load direction is an installation orientation of the inspection target when the inspection target substrate is installed on the stage 152. Next, the illumination condition (TTL illumination or oblique illumination) is selected (S703). In the case where the oblique illumination is selected, the spatial filters are set such as the installation positions and the number of spatial filters to be installed (S704), and then the illumination polarization is set. In the case where the TTL illumination is selected, the incidence angle of the TTL illumination is set (S705), the spatial filters are set such as the installation positions and the number of spatial filters to be installed (S706), the width of the specular reflection light blocking filter is set (S707), and then the illumination polarization is set (S708). After the illumination polarization is set, the detection condition of each detection unit is set (S709). The detection condition corresponds to the condition in the detection direction of a polarizer provided in each detection unit. Next, the illumination power is set (S710), and then the defect determination processing condition is set (S711). Accordingly, one inspection condition is set. In this case, a trial inspection of the inspection target substrate is carried out (S712), and the inspection results are displayed on the display unit (S713). The inspection results include the number of detected defects, whether or not each defect included in a set of defects preliminarily set as inspection target defects was detected, a capture rate, the number of pieces of misinformation, a misinformation rate, and the number of defects newly detected under the inspection conditions newly set as compared to a previously-set inspection recipe. The user determines the validity of the inspection conditions on the basis of these pieces of information (S714), and decides whether or not to add the inspection conditions to the inspection recipe (S715). In the case where the number of detected defects to be inspected and the detection capture rate reach targets using the inspection recipe updated in the above-described procedure (S716), the inspection recipe is determined (S717), and the setting of the inspection recipe is completed. In the case where the number of detected defects to be inspected and the detection capture rate do not reach targets, new inspection conditions are set again.

Figure 8:
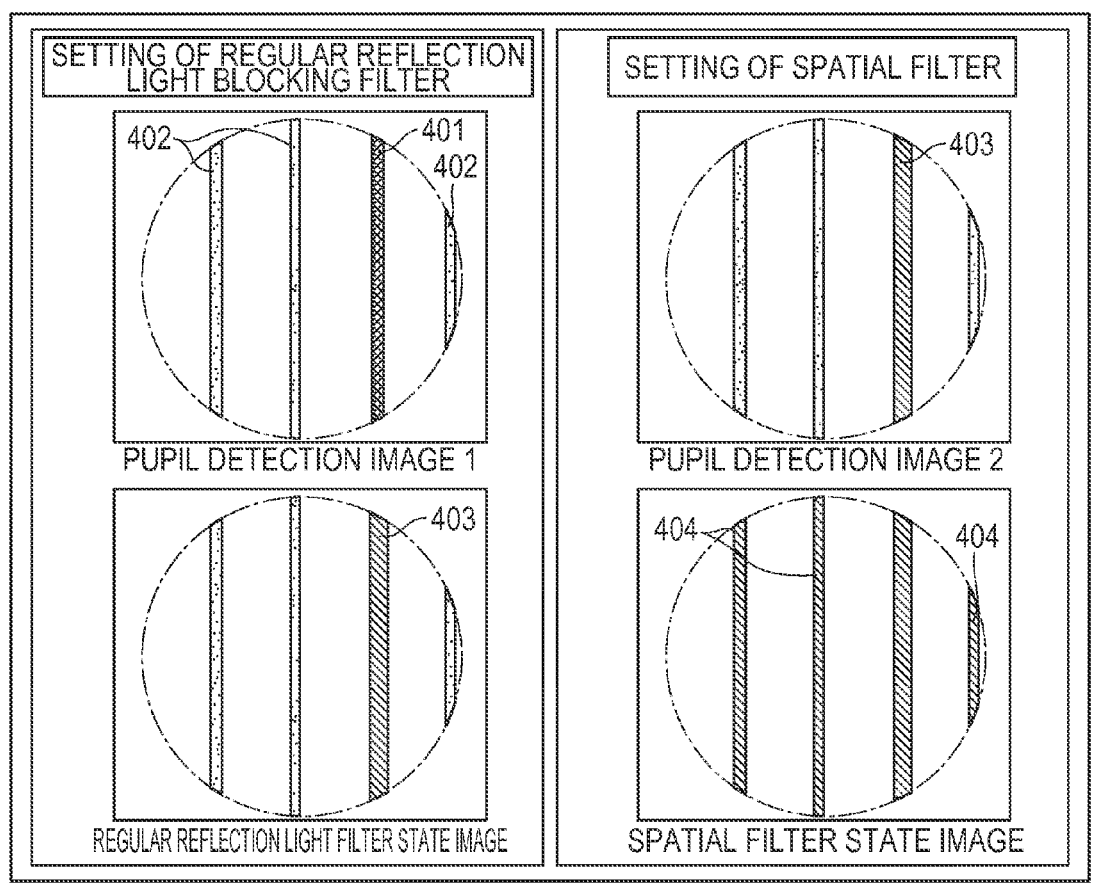
FIG. 8 shows an example of a GUI used for setting a specular reflection light filter and a spatial filter.

FIG. 8 shows an example of a GUI used for setting (S704, S706, and S707 of FIG. 7) the specular reflection light filter and the spatial filter. A pupil detection image 1 displays light intensity distribution of the pupil surface detected by the pupil detector. FIG. 8 shows examples of intensity distribution (on-pupil specular reflection light image 401) of the specular reflection light on the pupil surface, and intensity distribution (on-pupil diffracted light image 402) of the diffracted light of a repeated pattern on the pupil surface. The intensity and expansion width of the on-pupil specular reflection light image 401 are dependent on the material, film structure, and degree of roughness of the inspection target substrate. The intensity, expansion width, and distribution shape of the on-pupil diffracted light image 402 are dependent on the periodicity, shape, and degree of roughness of the repeated pattern on the inspection target substrate. It should be noted that the vertical direction corresponds to the X direction in the pupil surface, and the horizontal direction corresponds to the Y direction in the pupil surface in FIG. 8. A specular reflection light filter state image displays the state (position and width of the light-blocking area) of the specular reflection light filter. The pupil detection image 1 is stored in the memory unit 304 in a state where the specular reflection light image 401 prior to installation of the specular reflection light filter can be observed, and the display is fixed to the image. On the specular reflection light filter state image, the light intensity distribution of the pupil surface in a state where the specular reflection light filter is installed is displayed in real time, and a light-blocking area 403 of the specular reflection light filter is displayed as a dark area. The pupil detection image 1 and the specular reflection light filter state image are simultaneously displayed, so that the light-blocking area of the specular reflection light filter can be set so as to accurately block the specular reflection light.

On a pupil detection image 2, displayed is a light intensity distribution image of the pupil surface in a state where the specular reflection light filter is installed. The image is stored in the memory unit 304, and the display is fixed. The image is displayed in a state where the storage time, sensitivity, or display gain of the pupil detector are adjusted, so that the intensity distribution of the pattern diffracted light (zero-order diffracted light, namely, diffracted light components other than the specular reflection light) can be confirmed. The intensity of the pattern diffracted light is generally equal to or less than 10% of that of the specular reflection light. Thus, the pupil detection image 2 is displayed with a higher degree of sensitivity as compared to the pupil detection image 1. The storage time, sensitivity, or display gain of the pupil detector are adjusted in accordance with the diffracted light in a state where the specular reflection light filter is installed, so that the pattern diffracted light can be clearly observed using the pupil detector having a dynamic range (about 50 to 60 dB) same as a normal CCD camera without saturation of brightness of the specular reflection light area. On a spatial filter state image, the light intensity distribution of the pupil surface in a state where the specular reflection light filter and the spatial filter are installed is displayed in real time, and light-blocking areas of the specular reflection light filter and the spatial filter are displayed as dark areas. The pupil detection image 2 and the spatial filter state image are simultaneously displayed, so that a light-blocking area 404 of the spatial filter can be set so as to accurately block the pattern diffracted light.

Figure 9:
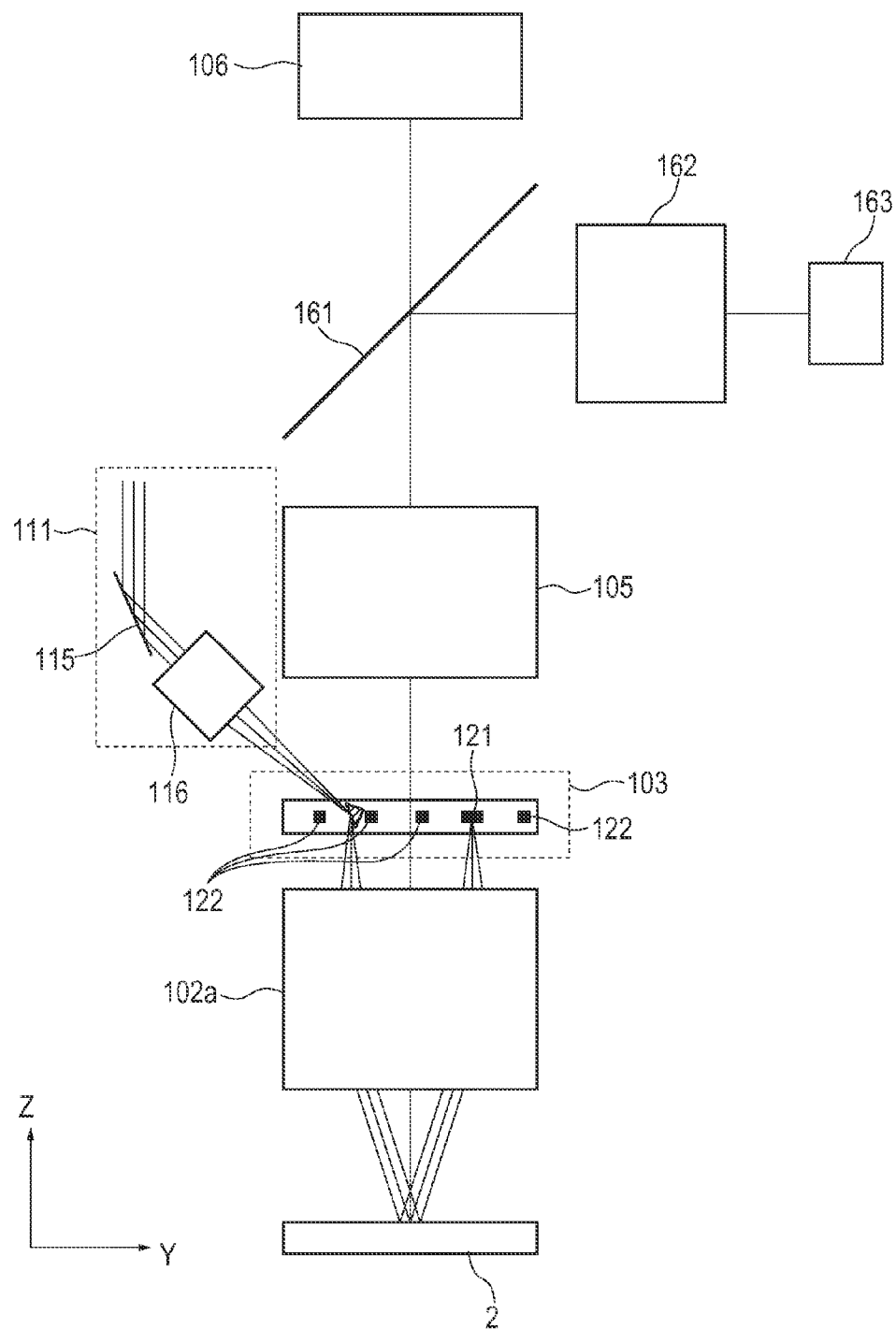
FIG. 9 shows a modification example of a configuration of TTL illumination.

FIG. 9 shows a modified example of a configuration of TTL illumination. In the configuration shown in FIG. 9, both of the TTL illumination mirror 121 and the objective pupil optical unit 103 are disposed on the pupil surface. The light flux from the TTL illumination unit 111 is allowed to enter from a direction inclined relative to the XY plane, so that part of the illumination light flux can be prevented from being blocked by the spatial filter 122. Further, the TTL illumination mirror is disposed in the pupil surface where the illumination light is condensed, so that the width of the TTL illumination mirror 121 in the Y direction can be narrowed, and the light-blocking area of the detection aperture by the TTL illumination mirror 121 can be narrowed. Thus, high imaging performance can be obtained.

It should be noted that the present invention is not limited to the above-described embodiment, and various modified examples may be included. For example, the above-described embodiment has been described in detail to plainly explain the present invention, and is not necessarily limited to one having the all configurations described above. Further, a part of the configuration in one embodiment can be replaced by a configuration of another embodiment, and the configuration in one embodiment can be added to another embodiment. In addition, a part of the configuration in each embodiment can be added to or replaced by another, or deleted.

Further, only the control lines and information lines that are assumed to be necessary for explanations are illustrated, and all of the control lines and information lines in a product are not necessarily illustrated. Almost all configurations may be regarded as being connected to each other in a real product.

LIST OF REFERENCE SIGNS

101 . . . light source unit
20 . . . processing unit
102 . . . objective lens
103 . . . objective pupil optical unit
105 . . . image forming lens
106 . . . detector
111 . . . TTL illumination unit
112 . . . oblique illumination unit
115 . . . mirror
116 . . . cylindrical lens
121 . . . TTL illumination mirror
122 . . . spatial filter
123 . . . specular reflection light filter
151 . . . stage driving unit
152 . . . X-Y-Z-θ stage
301 . . . entire control unit
302 . . . display unit
303 . . . computing unit
304 . . . memory unit

The invention claimed is:

1. A defect inspection device comprising:
an irradiation unit having a light source that emits a laser beam, a first light-condensing unit that linearly condenses the laser beam emitted from the light source, an objective pupil optical unit that allows the illumination light linearly condensed by the first light-condensing unit to pass through, and an objective lens that allows the illumination light having passed through the objective pupil optical unit to pass through;
an irradiation position control unit that controls a passing position of the illumination light in the objective pupil optical unit disposed at a pupil surface of the objective lens;
a detection unit having a second light-condensing unit that condenses light irradiated by the irradiation unit and generated from a sample, a specular reflection light-blocking unit that blocks specular reflection light from the sample and light components generated near the pupil surface among the light beams condensed by the second light-condensing unit, and an image forming unit that images the light that is condensed by the second light-condensing unit and that is not blocked by the specular reflection light-blocking unit into a detector; and
a defect determination unit that detects a defect on a surface of the sample on the basis of a signal of the image imaged by the image forming unit;
wherein the objective pupil optical unit includes a spatial filter disposed on the pupil surface of the objective lens of the irradiation unit, and an illumination mirror disposed at a position apart from the spatial filter by a predetermination distance; and wherein the spatial filter and the illumination mirror include angle rotation mechanisms.

2. The defect inspection device according to claim 1, wherein the objective pupil optical unit includes a mirror that condenses the illumination light from the light-condensing unit.

3. The defect inspection device according to claim 1, wherein the irradiation position control unit controls the passing position of the illumination light in the objective pupil optical unit by moving the mirror of the objective pupil optical unit and the light-condensing unit in a predetermined direction.

4. The defect inspection device according to claim 1, wherein the first light-condensing unit includes a TTL illumination unit.

5. The defect inspection device according to claim 1, wherein the objective lens of the irradiation unit and the second light-condensing unit of the detection unit are shared.

6. The defect inspection device according to claim 1, wherein a plurality of illumination units are provided.

7. A defect inspection device comprising:

an irradiation unit having a light source that emits a laser beam, a first light-condensing unit that linearly condenses the laser beam emitted from the light source, an objective pupil optical unit that allows the illumination light linearly condensed by the first light-condensing unit to pass through, and an objective lens that allows the illumination light having passed through the objective pupil optical unit to pass through;

an irradiation position control unit that controls a passing position of the illumination light in the objective pupil optical unit disposed at a pupil surface of the objective lens;

a detection unit having a second light-condensing unit that condenses light irradiated by the irradiation unit and generated from a sample, a specular reflection light-blocking unit that blocks specular reflection light from the sample and light components generated near the pupil surface among the light beams condensed by the second light-condensing unit, and an image forming unit that images the light that is condensed by the second light-condensing unit and that is not blocked by the specular reflection light-blocking unit into a detector; and a defect determination unit that detects a defect on a surface of the sample on the basis of a signal of the image imaged by the image forming unit wherein the objective pupil optical unit includes a specular reflection light filter that is disposed at a position where the specular reflection light from the sample is blocked;

wherein the specular reflection light filter includes a position adjusting mechanism that can adjust a light-blocking position; and wherein a light-blocking width is controlled by overlapping the plural specular reflection light filters with each other.

8. A defect inspection method comprising:

a light-emitting step of emitting a laser beam from a light source;

a first light-condensing step of linearly condensing the laser beam emitted in the light-emitting step;

an irradiation step of allowing the illumination light linearly condensed in the first light-condensing step to pass through a pupil surface of an objective lens and to reach onto a sample;

an irradiation position controlling step of controlling an irradiation position on the sample in the irradiation step to control a passing position of the illumination light on the pupil surface;

a second light-condensing step of condensing light irradiated in the irradiation step and generated from the sample;

a specular reflection light-blocking step of blocking specular reflection light from the sample and light components generated near the pupil surface among the light beams condensed in the second light-condensing step;

an image forming step of imaging the light that is condensed in the second light-condensing step and that is not blocked in the specular reflection light-blocking step into a detector; and a defect determination step of detecting a defect on a surface of the sample on the basis of a signal of the image imaged in the image forming step;

wherein a spatial filter is disposed on the pupil surface of the objective lens, and an illumination mirror is disposed at a position apart from the spatial filter by a predetermination distance; and wherein the spatial filter and the illumination mirror include angle rotation mechanisms.

* * * * *